United States Patent
Xu

(10) Patent No.: US 10,542,919 B2
(45) Date of Patent: Jan. 28, 2020

(54) METHOD AND SYSTEM FOR NON-INVASIVE BLOOD GLUCOSE DETECTION UTILIZING SPECTRAL DATA OF ONE OR MORE COMPONENTS OTHER THAN GLUCOSE

(75) Inventor: Zhi Xu, Saint Louis, MO (US)

(73) Assignee: St. Louis Medical Devices, Inc., Sunnyvale, CA (US)

( * ) Notice: Subject to any disclaimer, the term of this patent is extended or adjusted under 35 U.S.C. 154(b) by 499 days.

(21) Appl. No.: 12/407,999

(22) Filed: Mar. 20, 2009

(65) Prior Publication Data

US 2009/0247843 A1    Oct. 1, 2009

Related U.S. Application Data

(60) Provisional application No. 61/039,170, filed on Mar. 25, 2008.

(51) Int. Cl.
*A61B 5/1455* (2006.01)

(52) U.S. Cl.
CPC .................................. *A61B 5/1455* (2013.01)

(58) Field of Classification Search
CPC .......................... A61B 5/1455; A61B 5/14532
USPC ....... 600/316, 300, 301, 331, 310, 473, 319, 600/476, 583
See application file for complete search history.

(56) References Cited

U.S. PATENT DOCUMENTS

| | | |
|---|---|---|
| 3,910,701 A | 10/1975 | Henderson et al. |
| 3,954,560 A | 5/1976 | Delafosse et al. |
| 3,963,327 A | 6/1976 | Poirier |
| 4,014,321 A | 3/1977 | March |
| 4,632,559 A | 12/1986 | Brunsting |
| 4,655,225 A | 4/1987 | Dahne et al. |
| 4,781,195 A | 11/1988 | Martin |
| 4,962,311 A | 10/1990 | Poisel et al. |
| 4,997,769 A | 3/1991 | Lundsgaard et al. |
| 5,009,230 A | 4/1991 | Hutchinson |
| 5,028,787 A | 7/1991 | Rosenthal et al. |
| 5,077,476 A | 12/1991 | Rosenthal |

(Continued)

FOREIGN PATENT DOCUMENTS

| | | |
|---|---|---|
| CN | 1192665 | 9/1998 |
| CN | 2694097 Y | 4/2005 |

(Continued)

OTHER PUBLICATIONS

International Search Report for PCT/US2008/010670 dated Nov. 21, 2008.

(Continued)

*Primary Examiner* — Sean P Dougherty
*Assistant Examiner* — Benjamin S Melhus
(74) *Attorney, Agent, or Firm* — Haverstock & Owens LLP

(57) ABSTRACT

A method and system for detecting glucose in a biological sample is disclosed. This includes illuminating a biological sample with a light source, collecting transmitted, transflected or reflected light from the sample with a detector, generating spectral data of one or more components in the sample other than glucose in a spectral data analysis device, and analyzing the spectral data of the one or more components, sufficient to provide a glucose measurement from the spectral data of the one or more components other than glucose with the spectral data analysis device.

22 Claims, 8 Drawing Sheets

(56) References Cited

U.S. PATENT DOCUMENTS

| | | |
|---|---|---|
| 5,086,229 A | 2/1992 | Rosenthal et al. |
| 5,112,124 A | 5/1992 | Harjunmaa et al. |
| 5,137,023 A | 8/1992 | Mendelson et al. |
| 5,183,042 A | 2/1993 | Harjunmaa et al. |
| 5,222,496 A | 6/1993 | Clarke et al. |
| 5,255,171 A | 10/1993 | Clark |
| 5,282,473 A | 2/1994 | Braig et al. |
| 5,361,758 A | 11/1994 | Hall et al. |
| 5,423,983 A | 6/1995 | Chiang et al. |
| 5,448,992 A | 9/1995 | Kupershmidt |
| 5,501,648 A | 3/1996 | Grigoriev |
| 5,515,847 A | 5/1996 | Braig et al. |
| 5,522,388 A | 6/1996 | Ishikawa et al. |
| 5,529,065 A | 6/1996 | Tsuchiya |
| 5,535,743 A | 7/1996 | Backhaus et al. |
| 5,553,613 A | 9/1996 | Parker |
| 5,576,544 A | 11/1996 | Rosenthal |
| 5,615,672 A | 4/1997 | Braig et al. |
| 5,615,673 A | 4/1997 | Berger et al. |
| 5,666,956 A | 9/1997 | Buchert |
| 5,671,301 A | 9/1997 | Kupershmidt |
| 5,703,364 A | 12/1997 | Rosenthal |
| 5,743,262 A | 4/1998 | Lepper, Jr. et al. |
| 5,910,109 A | 6/1999 | Peters et al. |
| 6,025,597 A | 2/2000 | Sterling et al. |
| 6,043,492 A | 3/2000 | Lee et al. |
| 6,064,898 A * | 5/2000 | Aldrich .............. A61B 5/14532 600/316 |
| 6,067,463 A | 5/2000 | Jeng et al. |
| 6,097,975 A | 8/2000 | Petrovsky et al. |
| 6,134,458 A | 10/2000 | Rosenthal |
| 6,134,460 A | 10/2000 | Chance |
| 6,151,517 A | 11/2000 | Honigs et al. |
| 6,167,290 A | 12/2000 | Yang et al. |
| 6,181,958 B1 | 1/2001 | Steuer et al. |
| 6,205,354 B1 | 3/2001 | Gellermann et al. |
| 6,304,767 B1 | 10/2001 | Soller et al. |
| 6,312,393 B1 | 11/2001 | Abreu |
| 6,337,564 B2 | 1/2002 | Manzini et al. |
| 6,403,944 B1 | 6/2002 | MacKenzie et al. |
| 6,421,548 B1 | 7/2002 | Berman et al. |
| 6,424,848 B1 | 7/2002 | Berman et al. |
| 6,424,849 B1 | 7/2002 | Berman et al. |
| 6,424,851 B1 | 7/2002 | Berman et al. |
| 6,430,424 B1 | 8/2002 | Berman et al. |
| 6,445,938 B1 | 9/2002 | Berman et al. |
| 6,522,903 B1 | 2/2003 | Berman et al. |
| 6,574,490 B2 | 6/2003 | Abbink et al. |
| 6,671,528 B2 | 12/2003 | Steuer et al. |
| 6,684,099 B2 | 1/2004 | Ridder et al. |
| 6,723,048 B2 | 4/2004 | Fuller |
| 6,731,963 B2 | 5/2004 | Finarov et al. |
| 6,775,564 B1 | 8/2004 | Peters et al. |
| 6,804,002 B2 | 10/2004 | Fine et al. |
| 6,833,540 B2 | 12/2004 | MacKenzie et al. |
| 6,865,408 B1 | 3/2005 | Abbink et al. |
| 6,873,865 B2 | 3/2005 | Steuer et al. |
| 6,958,039 B2 | 10/2005 | Burd et al. |
| 6,968,222 B2 | 11/2005 | Burd et al. |
| 6,990,365 B1 | 1/2006 | Parker et al. |
| 6,993,372 B2 | 1/2006 | Fine et al. |
| 7,039,446 B2 * | 5/2006 | Ruchti ................. A61B 5/0071 600/310 |
| 7,039,447 B2 | 5/2006 | Berman et al. |
| 7,043,289 B2 | 5/2006 | Fine et al. |
| 7,107,087 B2 | 9/2006 | Hwang et al. |
| 7,133,711 B2 | 11/2006 | Chernoguz et al. |
| 7,215,987 B1 | 5/2007 | Sterling |
| 7,254,432 B2 | 8/2007 | Fine et al. |
| 7,266,400 B2 | 9/2007 | Fine et al. |
| 7,409,239 B2 | 8/2008 | Chung et al. |
| 7,424,317 B2 | 9/2008 | Parker et al. |
| 7,436,511 B2 | 10/2008 | Ruchti et al. |
| 7,809,418 B2 | 10/2010 | Xu |
| 7,961,305 B2 | 6/2011 | Xu et al. |
| 8,272,771 B2 | 9/2012 | Arai |
| 8,340,738 B2 | 12/2012 | Xu |
| 2001/0030742 A1 | 10/2001 | Kramer et al. |
| 2001/0039376 A1 | 11/2001 | Steuer et al. |
| 2001/0047137 A1 | 11/2001 | Moreno et al. |
| 2002/0010563 A1 | 1/2002 | Ratteree et al. |
| 2002/0016534 A1 | 2/2002 | Trepagnier et al. |
| 2002/0019055 A1 | 2/2002 | Brown et al. |
| 2002/0038080 A1 | 3/2002 | Makarewicz et al. |
| 2002/0091324 A1 * | 7/2002 | Kollias et al. ................ 600/476 |
| 2002/0161289 A1 | 10/2002 | Hopkins et al. |
| 2002/0167704 A1 | 11/2002 | Kleinhans et al. |
| 2003/0004423 A1 | 1/2003 | Lavie et al. |
| 2003/0023140 A1 | 1/2003 | Chance |
| 2003/0023152 A1 | 1/2003 | Abbink et al. |
| 2003/0055325 A1 | 3/2003 | Weber et al. |
| 2003/0078504 A1 | 4/2003 | Rowe |
| 2003/0099574 A1 | 5/2003 | Bentsen |
| 2004/0015734 A1 | 1/2004 | Rahman |
| 2004/0087844 A1 | 5/2004 | Yen |
| 2004/0106163 A1 | 6/2004 | Workman et al. |
| 2004/0127779 A1 | 7/2004 | Steuer et al. |
| 2004/0181132 A1 | 9/2004 | Rosenthal |
| 2004/0204865 A1 | 10/2004 | Lee et al. |
| 2004/0225205 A1 | 11/2004 | Fine et al. |
| 2004/0225206 A1 | 11/2004 | Kouchnir |
| 2005/0131286 A1 | 6/2005 | Parker et al. |
| 2005/0197790 A1 * | 9/2005 | Sterling et al. ................ 702/23 |
| 2005/0261560 A1 | 11/2005 | Ridder et al. |
| 2005/0272987 A1 | 12/2005 | Kiani-Azarbayjany et al. |
| 2005/0276072 A1 | 12/2005 | Hayashi et al. |
| 2006/0002598 A1 | 1/2006 | Rowe et al. |
| 2006/0004268 A1 | 1/2006 | Cho et al. |
| 2006/0009685 A1 | 1/2006 | Finarov et al. |
| 2006/0058622 A1 | 3/2006 | Tearney et al. |
| 2006/0063983 A1 * | 3/2006 | Yamakoshi ........ A61B 5/14532 600/310 |
| 2006/0129040 A1 | 6/2006 | Fine et al. |
| 2006/0152726 A1 | 7/2006 | Larsen et al. |
| 2006/0200014 A1 | 9/2006 | Fine et al. |
| 2006/0224057 A1 | 10/2006 | Burd et al. |
| 2006/0226992 A1 | 10/2006 | Al-Ali et al. |
| 2006/0234386 A1 | 10/2006 | Burns et al. |
| 2006/0250676 A1 | 11/2006 | Hagood |
| 2006/0258918 A1 | 11/2006 | Burd et al. |
| 2006/0264719 A1 | 11/2006 | Schurman et al. |
| 2007/0049811 A1 | 3/2007 | Kobayashi et al. |
| 2007/0078312 A1 | 4/2007 | Fine et al. |
| 2007/0112258 A1 | 5/2007 | Soyemi et al. |
| 2007/0149869 A1 | 6/2007 | Yen |
| 2008/0027297 A1 | 1/2008 | Yamakoshi |
| 2008/0137066 A1 | 6/2008 | Weinstein |
| 2008/0144004 A1 | 6/2008 | Rosenthal |
| 2008/0194014 A1 | 8/2008 | Young et al. |
| 2008/0266900 A1 | 10/2008 | Harbers et al. |
| 2008/0316488 A1 | 12/2008 | Mao |
| 2009/0059586 A1 | 3/2009 | Livesay et al. |
| 2009/0079964 A1 | 3/2009 | Xu |
| 2009/0105565 A1 | 4/2009 | Xu |
| 2009/0116017 A1 | 5/2009 | Xu et al. |
| 2009/0270700 A1 | 10/2009 | Van Herpen et al. |
| 2010/0026995 A1 | 2/2010 | Merritt et al. |
| 2013/0006070 A1 | 1/2013 | Xu |
| 2013/0006071 A1 | 1/2013 | Xu |
| 2013/0006072 A1 | 1/2013 | Xu |
| 2013/0006073 A1 | 1/2013 | Xu |

FOREIGN PATENT DOCUMENTS

| | | |
|---|---|---|
| CN | 1932840 A | 3/2007 |
| EP | 0160768 A1 | 11/1985 |
| EP | 0319159 A1 | 6/1989 |
| EP | 0781527 A1 | 7/1997 |
| EP | 01094745 A1 | 5/2001 |
| EP | 1281370 A2 | 2/2003 |
| EP | 1300712 A2 | 4/2003 |
| EP | 830582 B1 | 8/2005 |
| JP | 56-156138 A | 12/1981 |
| JP | 02-191434 A | 7/1990 |

(56) References Cited

FOREIGN PATENT DOCUMENTS

| | | | |
|---|---|---|---|
| JP | 07-088105 A | 4/1995 | |
| JP | 720551 U | 4/1995 | |
| JP | 9010238 | 1/1997 | |
| JP | H0956702 A | 3/1997 | |
| JP | 11037931 A | 2/1999 | |
| JP | 11-178813 A | 7/1999 | |
| JP | 2000083933 A | 3/2000 | |
| JP | 2003245265 A | 9/2003 | |
| JP | 2004267613 A | 9/2004 | |
| JP | 2004286475 A | 10/2004 | |
| JP | 2004290544 A | 10/2004 | |
| JP | 2004538054 A | 12/2004 | |
| JP | 2005-283563 A | 10/2005 | |
| JP | 2007185348 A | 7/2007 | |
| JP | 2009545344 A | 12/2009 | |
| RU | 2050545 C1 | 12/1995 | |
| RU | 2198402 C2 | 2/2003 | |
| SU | 1193541 A1 | 11/1985 | |
| WO | 90/13092 A1 | 11/1990 | |
| WO | 1991015991 A1 | 10/1991 | |
| WO | 1991015992 A1 | 10/1991 | |
| WO | 92/00513 A1 | 1/1992 | |
| WO | 1993000856 A1 | 1/1993 | |
| WO | 93/06774 A1 | 4/1993 | |
| WO | 9316629 A1 | 9/1993 | |
| WO | 1994013199 A1 | 6/1994 | |
| WO | 1994016614 A1 | 8/1994 | |
| WO | 95/05599 A1 | 2/1995 | |
| WO | 1995031930 A1 | 11/1995 | |
| WO | 1996004840 A1 | 2/1996 | |
| WO | 1996017546 A1 | 6/1996 | |
| WO | 96/39926 | 12/1996 | |
| WO | 96/41151 A1 | 12/1996 | |
| WO | 1996039927 A1 | 12/1996 | |
| WO | 1998003847 A2 | 1/1998 | |
| WO | 1998036681 A1 | 8/1998 | |
| WO | 99/16136 A1 | 4/1999 | |
| WO | 1999039631 A1 | 8/1999 | |
| WO | 2000001294 A1 | 1/2000 | |
| WO | 2000016688 A1 | 3/2000 | |
| WO | 01/16578 A1 | 3/2001 | |
| WO | 2001093755 A1 | 12/2001 | |
| WO | 2001096872 A2 | 12/2001 | |
| WO | 2002082990 A1 | 10/2002 | |
| WO | 2003010510 A2 | 2/2003 | |
| WO | 03/077756 A1 | 9/2003 | |
| WO | 2003079900 A1 | 10/2003 | |
| WO | 2005045377 A2 | 5/2005 | |
| WO | 2006086566 A2 | 8/2006 | |
| WO | 2006094109 A1 | 9/2006 | |
| WO | 2007122557 A2 | 11/2007 | |
| WO | 2008/039195 A1 | 4/2008 | |
| WO | 2009/035669 A1 | 3/2009 | |
| WO | 2009/045492 A1 | 4/2009 | |
| WO | 2010017238 A1 | 2/2010 | |

OTHER PUBLICATIONS

International Search Report for PCT/US2008/011438 dated Dec. 9, 2008.
Wagner et al., "Invasiveness as a Barrier to Self-Monitoring of Blood Glucose in Diabetes", Diabetes Technology & Therapeutics, Aug. 1, 2005.
Web Page Document entitled http://www.orsense.com/Diabetes_Monitoring dated Aug. 9, 2007.
Office Action for U.S. Appl. No. 12/256,028 dated Sep. 15, 2010.
Office Action for U.S. Appl. No. 12/209,807 dated Sep. 17, 2010.
International Preliminary Report on Patentability (Chapter II) for PCT/US2009/040942 dated Dec. 13, 2010.
International Preliminary Report on Patentability (Chapter II) for PCT/US2009/037805 dated Dec. 14, 2010.
International Preliminary Report on Patentability (Chapter II) for PCT/US2008/011438 dated Jun. 18, 2010.
International Search Report and Written Opinion for PCT/US2010/028255 dated May 19, 2010.
Office Action for U.S. Appl. No. 12/256,028 dated May 24, 2010.
Office Action for U.S. Appl. No. 12/209,807 dated May 17, 2010.
Office Action for RU Application 2010117396 dated Jun. 18, 2012.
Office Action for CN Application 200980126116.7 dated Jun. 4, 2012.
Office Action for RU Application 2010114587 dated Jun. 22, 2012.
Office Action for U.S. Appl. No. 12/425,535 dated May 16, 2012.
Office Action for CN Application 200880114960.3 dated Aug. 2, 2012.
Office Action for U.S. Appl. No. 12/729,886 dated Oct. 2, 2012.
Office Action for CN Application 201080022242.0 dated Jul. 4, 2013.
Extended European Search Report for EP Application 09751083.8 dated Jul. 26, 2013.
Office Action for AU Application 2010232841 dated Aug. 13, 2013.
Office Action for JP Application 2011-501936 dated Jun. 25, 2013.
Office Action for JP Application 2010-524873 dated Dec. 25, 2012.
Office Action for JP Application 2010-527994 dated Dec. 25, 2012.
Office Action for CN Application 200880114960.3 dated Jan. 29, 2013.
Office Action for U.S. Appl. No. 12/729,886 dated Mar. 12, 2013.
Office Action for CN Application 200980126116.7 dated Feb. 16, 2013.
Office Action for U.S. Appl. No. 12/425,535 dated Mar. 22, 2012.
Extended European Search Report for EP Application 08830786.3 dated Apr. 22, 2013.
Office Action for RU Application 2010152373 dated Mar. 26, 2013.
Examiner's Decision of Rejection for JP Application 2010-527994 dated Dec. 10, 2103.
Office Action for AU Application 2008299938 dated Sep. 13, 2013.
Office Action for CN Application 200980126116.7 dated Oct. 17, 2013.
Office Action for JP Application 2010-524873 dated Nov. 19, 2013.
Office Action for JP Application 2011-510533 dated Dec. 3, 2013.
Office Action for CA Application 2700996 dated Jul. 30, 2014.
Office Action for JP Application 2011-501936 dated Aug. 5, 2014.
Office Action for RU Application 2010114587 dated Mar. 25, 2014.
Office Action for EP Application 08830786.3 dated Jan. 10, 2014.
Office Action for CN Application 201210419849.3 dated Jan. 6, 2014.
Office Action for CN Application 201210420843.8 dated Feb. 17, 2014.
Office Action for CN Application 201210419740.X dated Feb. 28, 2014.
Office Action for EP Application 09751083.8 dated Mar. 28, 2014.
Office Action for CN Application 201080022242.0 dated Mar. 12, 2014.
Office Action for CA Application 2699626 dated Feb. 27, 2015.
Office Action for CN Application 200880114960.3 dated Feb. 17, 2015.
Office Action for CN Application 201310489245.0 dated Feb. 26, 2015.
Office Action for U.S. Appl. No. 13/610,342 dated Jan. 21, 2015.
Office Action for U.S. Appl. No. 13/610,140 dated Jan. 21, 2015.
Office Action for U.S. Appl. No. 13/610,256 dated Jan. 21, 2015.
Office Action for U.S. Appl. No. 13/610,423 dated Jan. 22, 2015.
Office Action for U.S. Appl. No. 13/610,387 dated Jan. 22, 2015.
Office Action for CN Application 201210420830.0 dated Jan. 5, 2015.
Office Action for CN Application 201310489245.0 dated Jan. 25, 2016.
Office Action for JP Application 2014-245584 dated Jan. 5, 2016, includes English translation.
Office Action for EP Application 9751083.8 dated Jan. 26, 2016.
Extended European Search Report for EP Application 08836010.2 dated Mar. 8, 2016.
Office Action for U.S. Appl. No. 13/610,423 dated Mar. 24, 2016.
Attached please find the Office Action dated Jun. 30, 2017 for the Indian application No. 4886/KOLNP/2010.
European Search Report from European Application No. 17159427.8.

(56) References Cited

OTHER PUBLICATIONS

Texas Instruments TSL260, TSL261, TSL262, IR Light-To-Voltage Optical Sensors 1993.
European First Examination Report dated Jun. 4, 2018. EP Application No. 10759220.6.
Indian Examination Report dated Apr. 13, 2018, Application No. 4144/KOLNP/2011.
First Examination Report dated Oct. 27, 2017 for the Indian Application No. 1186/KOLNP/2010.
Office Action dated May 21, 2019 for Brazilian Patent Application No. PI0909825-9.

* cited by examiner

METHOD AND SYSTEM FOR NON-INVASIVE BLOOD GLUCOSE DETECTION UTILIZING SPECTRAL DATA OF ONE OR MORE COMPONENTS OTHER THAN GLUCOSE

CROSS-REFERENCE TO RELATED APPLICATION

This patent application claims priority to U.S. Provisional Patent Application Ser. No. 61/039,170 filed Mar. 25, 2008, the disclosure of which is incorporated herein by reference.

BACKGROUND OF THE INVENTION

Diabetes is a chronic disease that, when not controlled, over time leads to serious damage to many of the body's systems, including the nerves, blood vessels, eyes, kidneys and heart. The National Institute of Diabetes and Digestive and Kidney Diseases (NIDDK) estimates that 23.6 million people or 7.8 percent of the population in the United States have diabetes in 2007. Globally, the World Health Organization (WHO) estimates that more than 180 million people have diabetes, a number they expect to increase to 366 million by 2030, with 30.3 million in the United States. According to the WHO, an estimated 1.1 million people died from diabetes in 2005. They project that diabetes deaths will increase by more than 50% between 2006 and 2015 overall and by more than 80% in upper-middle income countries.

The economic burden from diabetes for individuals and society as a whole is substantial. According to the American Diabetes Association, the total annual economic cost of diabetes was estimated to be $174 billion in the United States in 2007. This is an increase of $42 billion since 2002. This 32% increase means the dollar amount has risen over $8 billion more each year.

A vital element of diabetes management is the self-monitoring of blood glucose (SMBG) concentration by diabetics in the home environment. By testing blood glucose levels often, diabetics can better manage medication, diet and exercise to maintain control and prevent the long-term negative health outcomes. In fact, the Diabetes Control and Complications Trial (DCCT), which followed 1,441 diabetics for several years, showed that those following an intensive-control program with multiple blood sugar tests each day as compared with the standard-treatment group had only one-fourth as many people develop diabetic eye disease, one-half as many develop kidney disease, one-third as many develop nerve disease, and far fewer people who already had early forms of these three complications got worse.

However, current monitoring techniques discourage regular use due to the inconvenient and painful nature of drawing blood through the skin prior to analysis, which causes many diabetics to not be as diligent as they should be for good blood glucose control. As a result, non-invasive measurement of glucose concentration is a desirable and beneficial development for the management of diabetes. A non-invasive monitor will make testing multiple times each day pain-free and more palatable for children with diabetes. According to a study published in 2005 (J. Wagner, C. Malchoff, and G. Abbott, Diabetes Technology & Therapeutics, 7(4) 2005, 612-619), people with diabetes would perform SMBG more frequently and have improved quality of life with a non-invasive blood glucose monitoring device.

Currently, there remains a concentrated effort in academia and industry to develop reliable, affordable non-invasive blood glucose monitors. One technique of non-invasive blood chemicals detection involves collecting and analyzing light spectra data. Extracting information about blood characteristics such as glucose concentration from spectral or other data obtained from spectroscopy is a complex problem due to the presence of components (e.g., skin, fat, muscle, bone, interstitial fluid) other than blood in the area that is being sensed. Such other components can influence these signals in such a way as to alter the reading. In particular, the resulting signal may be much larger in magnitude than the portion of the signal that corresponds to blood and therefore limits the ability to accurately extract blood characteristics information.

The prevailing view is to correlate the change in optical absorption at certain wavelengths with blood glucose concentration, while ignoring the fact that similar changes in optical absorption could also be caused by other factors, such as physical exercise, medication, emotion, or a change in body chemistry, such as endocrine levels, etc. As such, good correlations obtained in well controlled laboratory conditions do not translate into successful, reliable market devices.

The present invention is directed to overcoming one or more of the problems set forth above.

SUMMARY OF INVENTION

Embodiments of the present invention relate to a method for detecting glucose in a biological sample. The method includes illuminating a biological sample with a light source, collecting transmitted, transflected or reflected light from the sample, generating spectral data of one or more components in the sample other than glucose and analyzing the spectral data of the one or more components sufficient to provide a glucose concentration measurement from the spectral data of the one or more components other than glucose.

These are merely some of the innumerable aspects of the present invention and should not be deemed an all-inclusive listing of the innumerable aspects associated with the present invention.

BRIEF DESCRIPTION OF THE DRAWINGS

For a better understanding of the present invention, reference may be made to accompanying drawings, in which.

DETAILED DESCRIPTION OF THE INVENTION

In the following detailed description, numerous exemplary specific details are set forth in order to provide a thorough understanding of the invention. However, it will be understood by those skilled in the art that the present invention may be practiced without these specific details, or with various modifications of the details. In other instances, well known methods, procedures, and components have not been described in detail so as not to obscure the present invention.

Embodiments of the invention relate to a method for non-invasive blood glucose detection. Glucose has extremely weak optical absorption in the visible (Vis) and near infrared (NIR) regions from about 400 nm to about 2500 nm. It is very difficult to accurately determine the concentration of glucose in a biological sample by determining the portion of optical absorption generated by glucose in the biological sample, because the portion of optical absorption by other components is typically several orders of magnitude larger than that directly by glucose in the two wavelength regions. But, glucose can induce changes in the optical absorption of other components in the sample, such as hemoglobin or water. These changes in optical absorption of components other than glucose can be used to indirectly determine the concentration of glucose in a biological sample.

Figure 1:
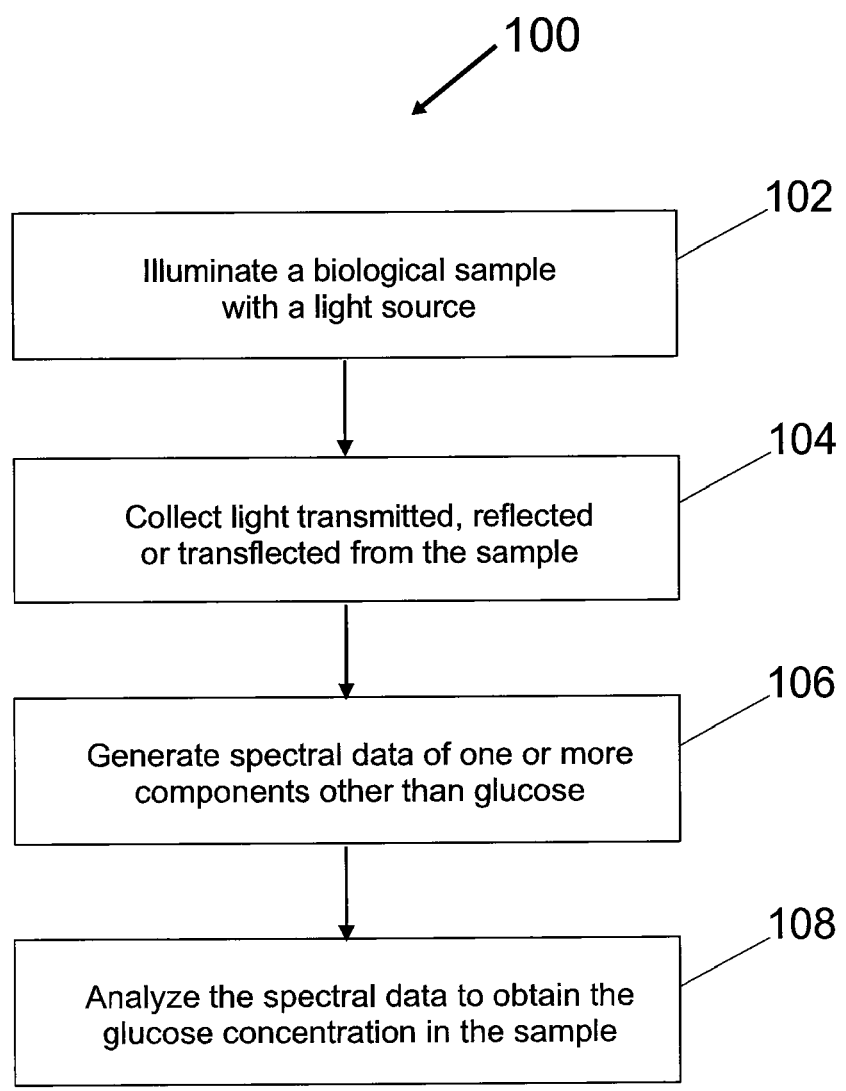
FIG. 1 illustrates a block flow diagram of a method for detecting glucose in a biological sample, according to some embodiments.

Referring to FIG. 1, a block flow diagram of a method for detecting glucose in a biological sample is shown, according to some embodiments and is generally indicated by numeral 100. In the description of the flowcharts, the functional explanation marked with numerals in angle brackets <nnn>, will refer to the flowchart blocks bearing that numeral. A biological sample maybe illuminated with a light source <102>. Transmitted, transflected or reflected light may then be collected from the sample <104>. Spectral data of one or more components in the sample other than glucose may be generated <106>. The spectral data of the one or more components may be analyzed, sufficient to provide a glucose concentration measurement from the spectral data of the one or more components other than glucose <108>.

Illuminating <102> may refer to exposing the biological sample to a light source in the visible (Vis), near infrared (NIR) or mid-infrared spectral regions. The wavelength range for illumination <102> may occur between about 400 nm and about 10,000 nm, for example. The illuminating <102> may occur between about 400 nm and about 2500 nm or about 400 nm and about 1000 nm, for example. The light source may be lasers, light emitting diodes (LED), incandescent lamps, halogen lamps or a combination thereof, for example. The light source may be a plurality of lasers. Prior to or after illumination of the sample <102>, a reference sample may be illuminated for calibration.

The biological sample may be any portion of the human body that contains glucose or has the potential to contain glucose. The biological sample may be a human finger, toe, ear lobe, tongue or arm, for example.

After illumination <102>, transmitted, transflected or reflected light may then be collected from the sample <104>. The light may be collected by one or more detectors or light-sensing devices. An array of photodiodes may be utilized, for example.

Spectral data of one or more components in the sample other than glucose may be generated <106>. The detector may generate a corresponding current signal that is proportional to the power of the light received by the detector. The current signal generated by the detector can be converted to another form of signal, such as an analog voltage signal or a digital signal. Such signals may be converted to spectral or absorbance data using known processors and algorithms.

The spectral data of the one or more components may be analyzed <108>, sufficient to provide a glucose concentration measurement from the spectral data of the one or more components other than glucose.

Spectroscopic data generation <106> and analysis <108> may be carried out using a pulsatile or a stationary methodology.

A pulsatile data generation and analysis methodology has been described in presently owned U.S. patent application Ser. No. 12/245,298, filed Oct. 3, 2008, which is incoporated herein by reference and U.S. patent application Ser. No. 12/209,807, filed Sep. 12, 2008, which is incoporated herein by reference. When light is transmitted through a biological sample, such as a human finger, the light is absorbed and scattered by various components of the finger including muscle, bone, fat and blood. It has been observed, however, that light absorption by a human finger exhibits a small cyclic pattern that corresponds to a heartbeat.

Figure 2A:
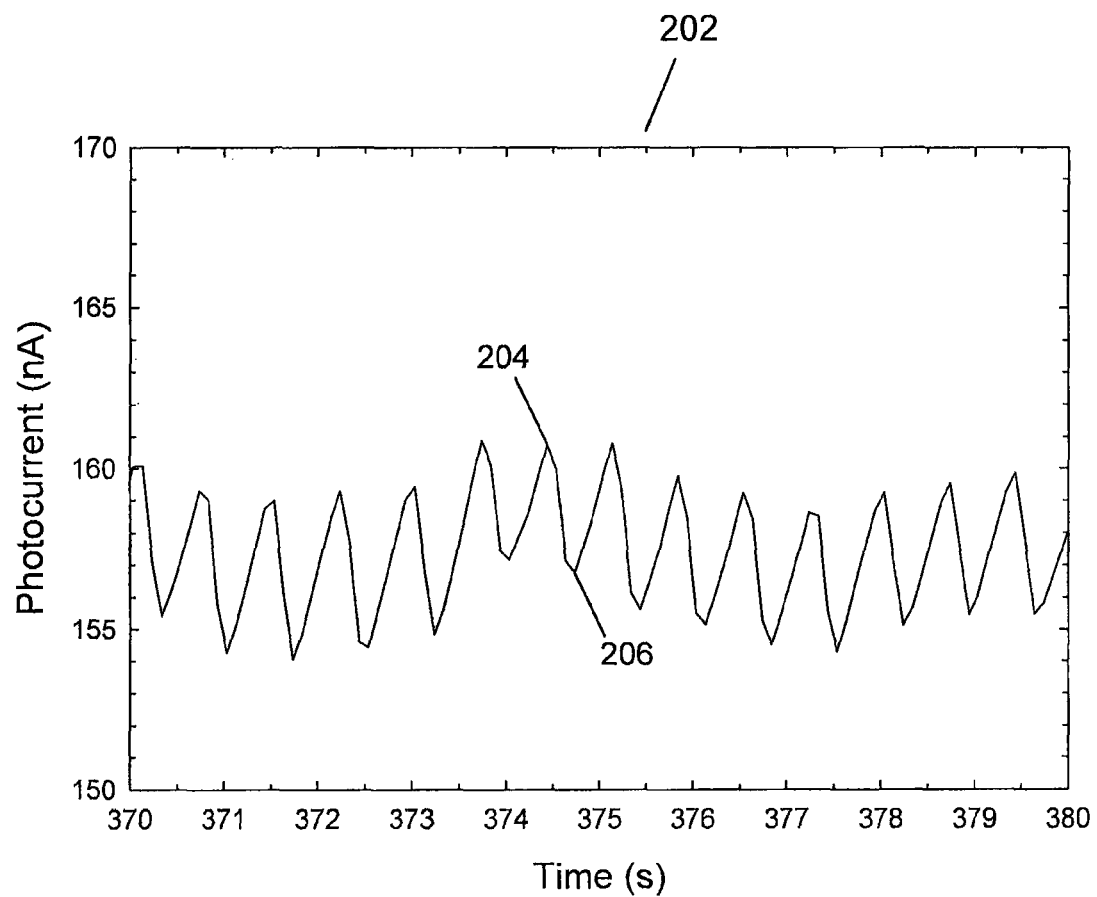
FIGS. 2A and 2B illustrate plots of a pulse wave corresponding to light absorption of arterial blood in a human finger, according to some embodiments.
Figure 2B:
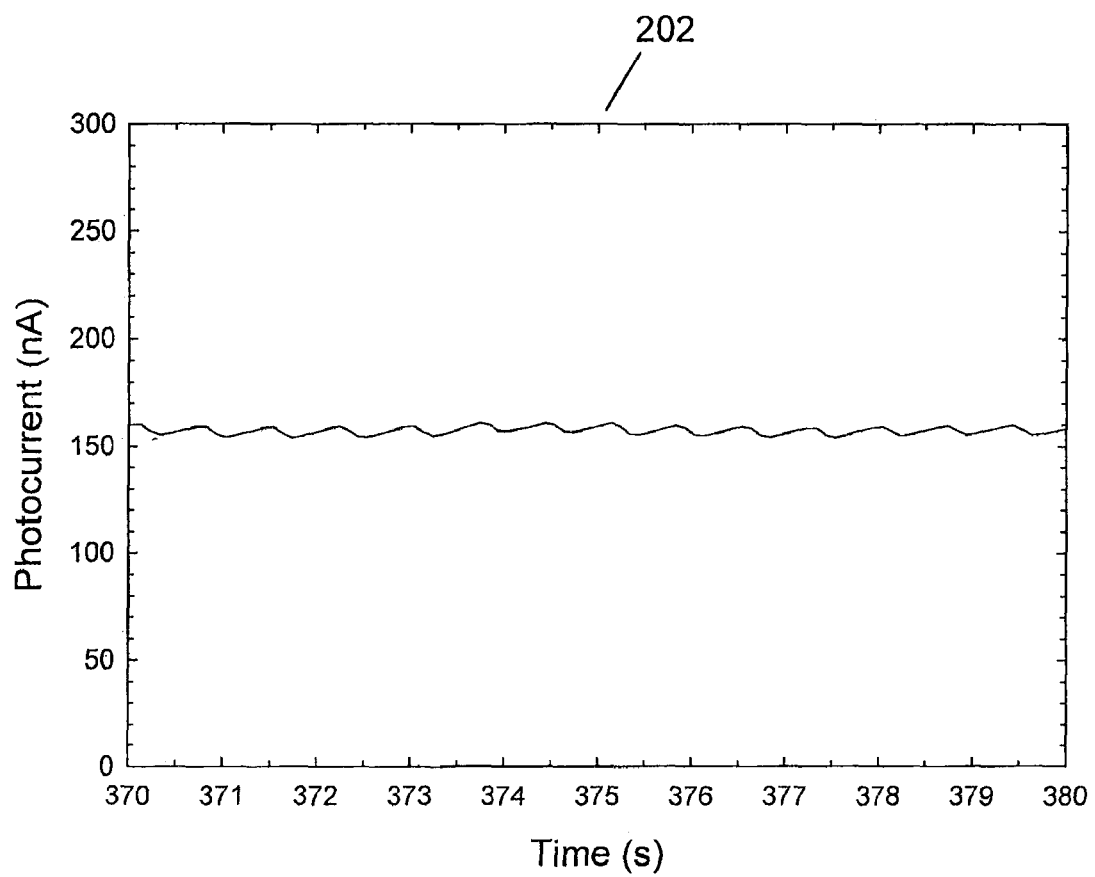

FIG. 2A depicts a plot 202 of a pulse wave that corresponds to the light absorption of arterial blood in the capillary due to the heartbeat of the user. Although the magnitude of the cyclic pattern is small in comparison to the total photocurrent generated by the detector, considerable information can be extracted from the cyclic pattern of the plot 202. For example, assuming that the person's heart rate is sixty beats per minute, the time between the start of any pulse beat and the end of that pulse beat is one second. During this one-second period, the plot will have a maximum or peak 204 reading and minimum or valley 206 reading. The peak 204 reading of the plot corresponds to when there is a minimum amount of blood in the capillaries, and the valley 206 reading corresponds to when there is a maximum amount of blood in the capillaries. By using optical information provided by the peak and valley of the cyclic plot, the major constituents that are in the body that are not in the capillaries, such as fat, muscle (i.e., protein) and interstitial fluid, are excluded. These major constituents that are not in the capillaries are excluded because they are not likely to change during the one-second interval. In other words, the light that is impeded by the blood can be detected based on the peaks and valleys of the plot 202. FIG. 2A illustrates the cyclic pattern on a magnified scale. FIG. 2B depicts a more accurate reflection of the cyclic pattern in terms of signal amplitude.

In a stationary data acquisition and analysis methodology, the light absorption is averaged over a period of time to remove the fluctuation in light absorption due to the heart beat. The glucose concentration can be extracted from the averaged light absorption at different wavelengths over the same period of data acquisition time.

Referring again to FIG. 1, analyzing <108> may also include mathematically comparing the changes in absorbance of the one or more components to changes in glucose concentration. Analyzing <108> may include eliminating spectral data of the one or more components for changes in absorbance not related to interactions with glucose.

Because glucose in the biological sample has such a weak optical signal in the Vis and NIR spectral range, the methods of the present invention do not attempt to analyze the glucose signal. Glucose does physically or chemically interact with one or more components in the blood and induce changes in the optical signal of these components as a function of glucose concentration. By analyzing the changes in the one or more components, the concentration of glucose in the sample may be determined.

EXAMPLE

Figure 3:
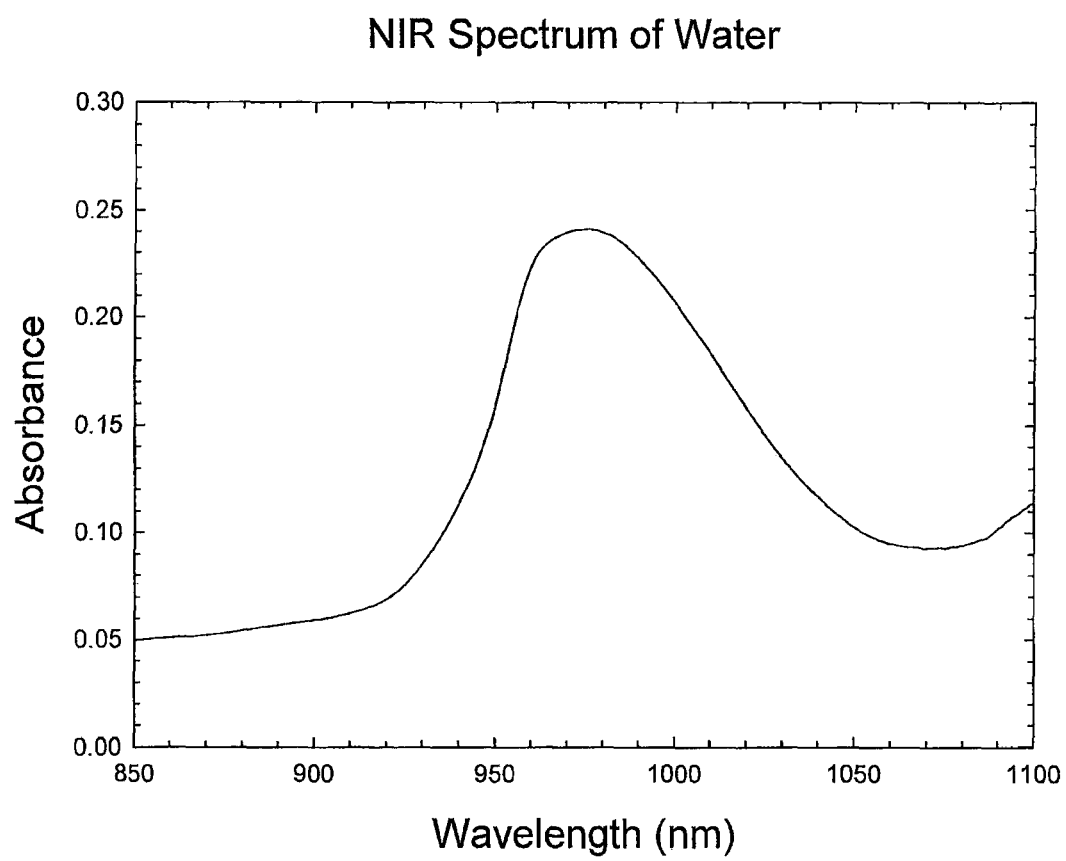
FIG. 3 illustrates a graphical view of a water absorbance spectrum, according to some embodiments.

FIG. 3 shows the NIR spectrum of water between 850 nm to 1100 nm. A strong positive peak is seen between about 920 nm and 1070 nm. The spectrum was taken with a Perkin-Elmer™ Lambda-14™ Double Beam UV-Vis-NIR (190 nm to 1100 nm) spectrometer. The scanning speed was 30 nm/min, the spectrum resolution was 4 nm, and one data point was collected per nm. The reference was the air and the sample was HPLC grade water in a quartz cuvette with 1 cm light path. The baseline absorbance of the spectrum, about 0.05, is due to reflections from two air/quartz interfaces and two water/quartz interfaces.

Figure 4:
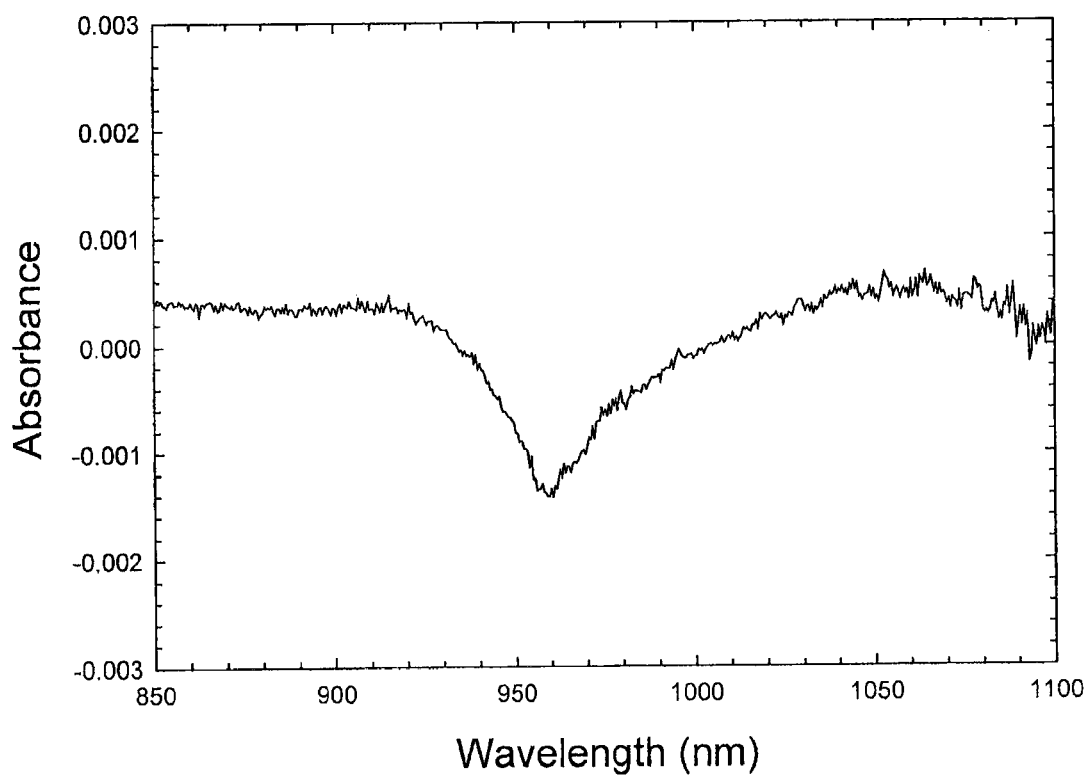
FIG. 4 illustrates a graphical view of an absorbance spectrum of a 1250 mg/dL glucose solution, according to some embodiments.
Figure 5:
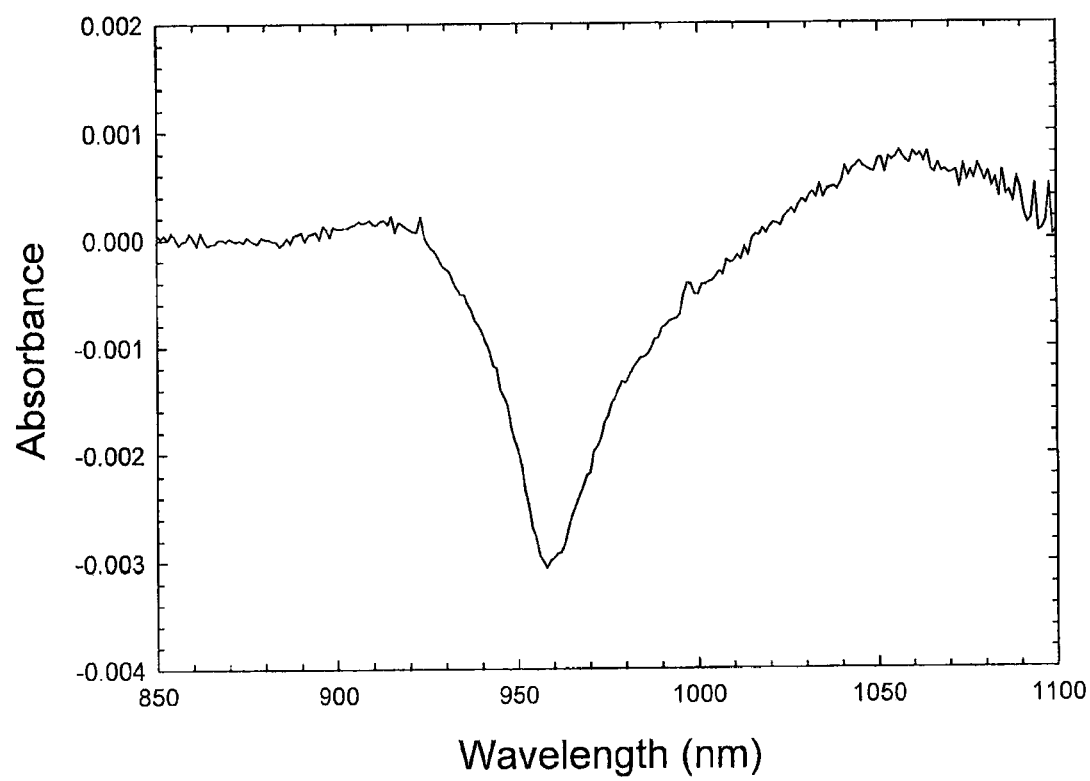
FIG. 5 illustrates a graphical view of an absorbance spectrum of a 2500 mg/dL glucose solution, according to some embodiments.

FIG. 4 shows the absorbance spectrum of a 1250 mg/dL solution of alfa-D(+)-glucose in HPLC grade water, and FIG. 5 shows the absorbance spectrum a 2500 mg/dL solution of alfa-D(+)-glucose in HPLC grade water. The two spectra were taken under the same condition as the water spectrum in FIG. 3, except that the quartz cuvette containing HPLC grade water was used as the reference. To minimize the effect of temperature on water absorption, the two glucose solutions and HPLC grade water were equilibrated in the sample chamber of the spectrometer for four hours before the measurements.

Figure 6:
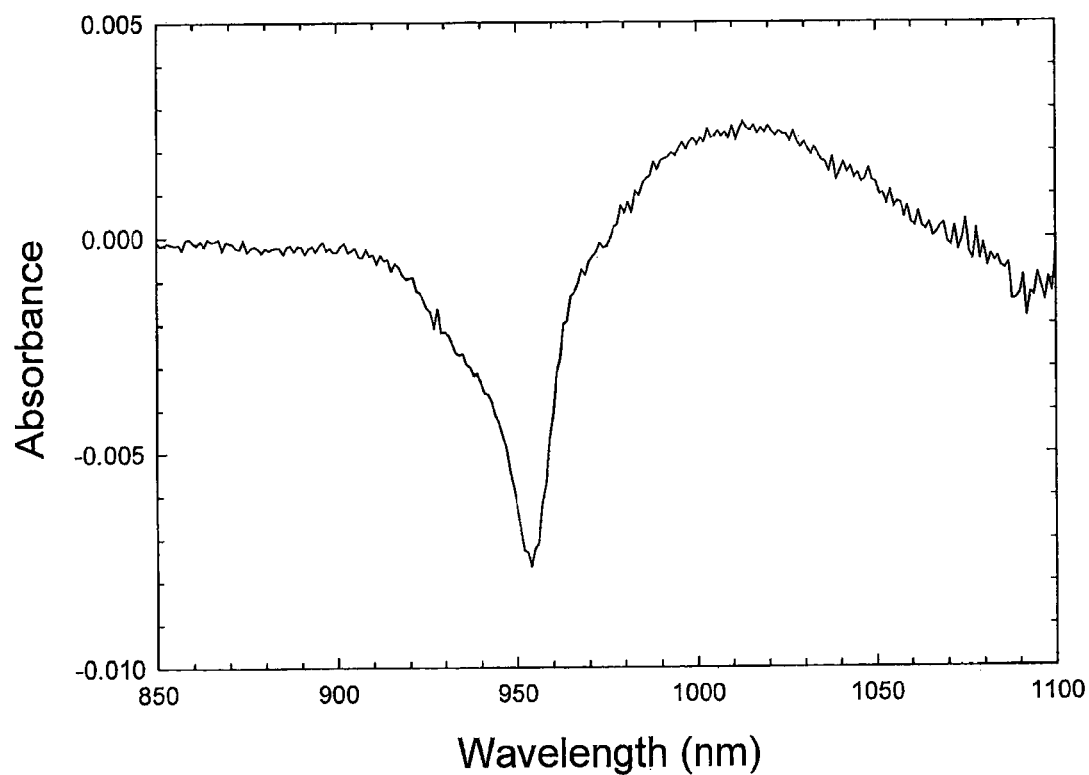
FIG. 6 illustrates a graphical view of differential water spectrum, according to some embodiments.

Both FIG. 4 and FIG. 5 show a large negative peak at about 960 nm, about −0.0018 for the 1250 mg/dL glucose solution and about −0.0030 for the 2500 mg/dL glucose solution. This negative peak is not caused by the optical absorption of glucose in this region. Instead, it is a result of change in water absorption due to the presence of glucose. This is supported by the simulated differential water spectrum in FIG. 6. The simulated differential water spectrum was obtained by manually red shifting 1 nm of all data points in the water spectrum of FIG. 3, then subtracting the original water spectrum from the red shifted spectrum. FIG. 6 shows a negative peak centered at 960 nm with a very similar peak shape as those of FIG. 4 and FIG. 5.

Figure 7:
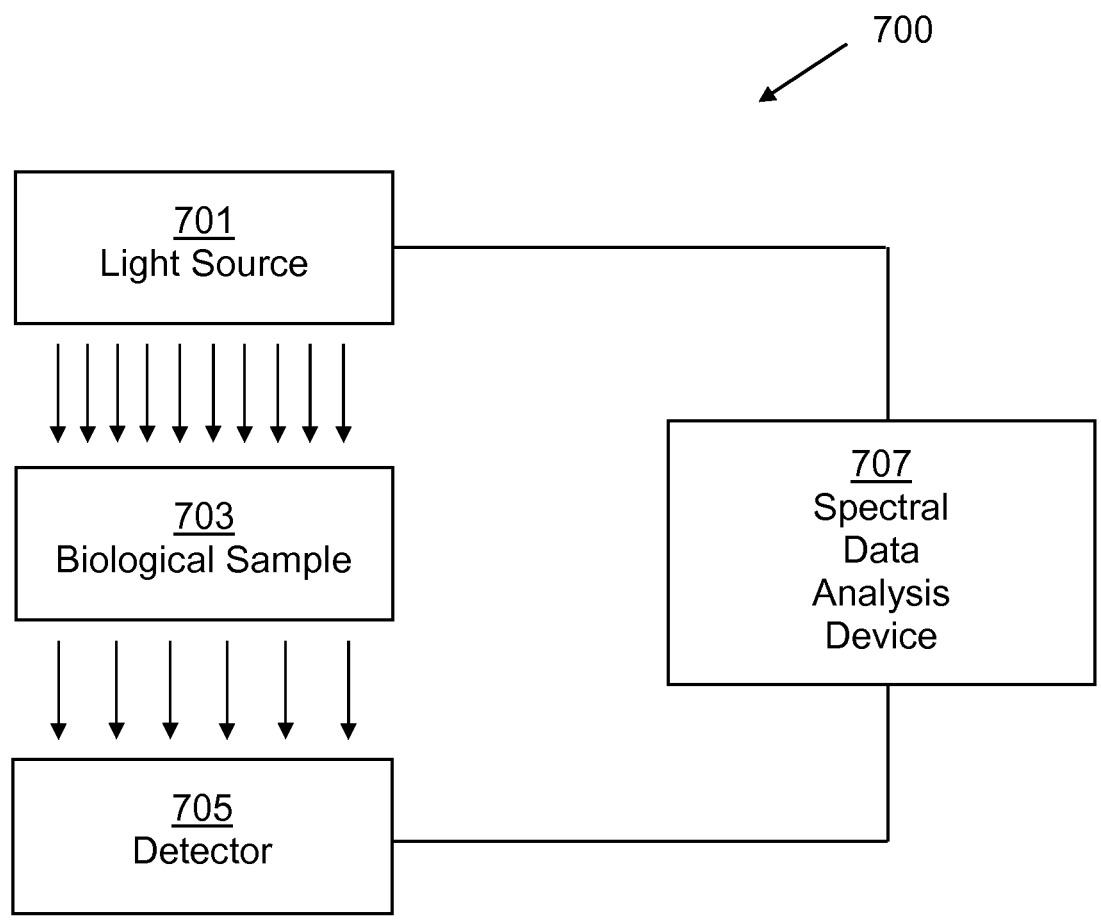
FIG. 7 illustrates a system for detecting glucose in a biological sample, according to some embodiments.

FIG. 7 shows an exemplary system for conducting an embodiment of the present invention that is generally indicated by numeral 700. The system of FIG. 7 comprises a light source 701, biological sample 703, detector 705, and spectral data analysis device 707. A light source 701 maybe lasers, light emitting diodes (LED), incandescent lamps, halogen lamps or a combination thereof, for example. The light source may be a plurality of lasers. A biological sample 703 may be a human finger, toe, ear lobe, tongue or arm. A detector 705 may be any of a wide variety of light detectors with an illustrative, but nonlimiting, example being an array of photodiodes. Spectral data analysis device 707 may be any device capable of analyzing spectral data as described herein. An illustrative, but nonlimiting, example of a spectral data analysis device 707 may include an SR760™ from Stanford Research Systems, which is a single-channel 100 kHz FFT spectrum analyzers with a dynamic range of 90 dB and a real-time bandwidth of 100 kHz.

Thus, there has been shown and described several embodiments of a novel invention. As is evident from the foregoing description, certain aspects of the present invention are not limited by the particular details of the examples illustrated herein, and it is therefore contemplated that other modifications and applications, or equivalents thereof, will occur to those skilled in the art. The terms "have," "having," "includes" and "including" and similar terms as used in the foregoing specification are used in the sense of "optional" or "may include" and not as "required." Many changes, modifications, variations and other uses and applications of the present construction will, however, become apparent to those skilled in the art after considering the specification and the accompanying drawings. All such changes, modifications, variations and other uses and applications which do not depart from the spirit and scope of the invention are deemed to be covered by the invention which is limited only by the claims that follow.

The invention claimed is:

1. A method for detecting blood glucose in a biological sample, comprising:
    illuminating a biological sample with a light source;
    collecting transmitted, transflected or reflected light from the sample with a detector;
    generating spectral data, having peaks and valleys, of one or more blood components in the sample other than blood glucose in a spectral data analysis device; and
    analyzing the spectral data of the one or more blood components, wherein the one or more blood components are non-blood glucose, to provide a blood glucose measurement with the spectral data analysis device by measuring light absorption based on the peaks and the valleys of the spectral data, which excludes an interference of a measurement by fat, muscle, and interstitial fluid, without analyzing a glucose signal, wherein the light absorption measured of the one or more blood components that are non-blood glucose contains a change of an absorption amount that is induced by an amount of a presence of the blood glucose which is used to indirectly determine a concentration of the blood glucose.

2. The method of claim 1, further comprising before or after illuminating, calibrating a light source to a reference sample.

3. The method of claim 1, wherein the light source comprises lasers, light emitting diodes, halogen lamps, incandescent lamps or a combination thereof.

4. The method of claim 1, wherein illuminating comprises exposing the biological sample to a light source in at least one of the near infrared, mid-infrared and visible light regions.

5. The method of claim 1, wherein illuminating comprises exposing the biological sample to a light source in the range of 400 nm to 2500 nm.

6. The method of claim 1, wherein collecting comprises collecting transmitted, transflected or reflected light with the detector.

7. The method of claim 1, wherein analyzing spectral data comprises performing a pulsation analysis on the spectral data.

8. The method of claim 1, wherein analyzing spectral data comprises performing a stationary analysis on the spectral data.

9. The method of claim 1, wherein analyzing comprises mathematically comparing the changes in absorbance of the one or more blood components to changes in blood glucose concentration.

10. The method of claim 1, wherein analyzing comprises eliminating spectral data of the one or more blood components for changes in absorbance not related to interactions with blood glucose.

11. The method of claim 1, wherein the biological sample comprises a portion of at least one of a human finger, toe, ear lobe, tongue and arm.

12. A system for detecting blood glucose in a biological sample, comprising:
    a light source configured to illuminate a biological sample comprising a plurality of blood components, the blood components comprising blood glucose and at least one blood component other than blood glucose;
    a detector configured to collect transmitted, transflected or reflected light from the biological sample; and a computing device configured to (1) generate spectral data of one or more blood components in the biological sample, wherein the one or more blood components are non-blood glucose, and (2) analyze the spectral data of the one or more blood components that are non-blood glucose to provide a blood glucose measurement by measuring light absorption based on the peaks and the valleys of the spectral data, which excludes an interference of a measurement by fat, muscle, and interstitial fluid, without analyzing a glucose signal, wherein the light absorption measured of the one or more blood components that are non-blood glucose contains a change of an absorption amount that is induced by an amount of a presence of the blood glucose which is used to indirectly determine a concentration of the blood glucose.

13. The system of claim 12, wherein the light source comprises lasers, light emitting diodes, halogen lamps, incandescent lamps or a combination thereof.

14. The system of claim 12, wherein the light source is configured to emit light in at least one of the near infrared, mid-infrared and visible light regions.

15. The system of claim 12, wherein the light source is configured to emit light having a wavelength in the range of 400 nm to 2500 nm.

16. The system of claim 12, wherein the detector is configured to collect transmitted, transflected or reflected light.

17. The system of claim 12, wherein the spectral data analysis device is configured to perform a pulsation analysis on the spectral data.

18. The system of claim 12, wherein the spectral data analysis device is configured to perform a stationary analysis on the spectral data.

19. The system of claim 12, wherein the spectral data analysis device is configured to mathematically compare the changes in absorbance of the one or more blood components to changes in blood glucose concentration.

20. The system of claim 12, wherein the spectral data analysis device is configured to eliminate portions of the spectral data that are attributable to changes in absorbance not related to interactions with blood glucose.

21. The system of claim 12, wherein the biological sample comprises a portion of at least one of a human finger, toe, ear lobe, tongue and arm.

22. The method of claim 1, wherein the interference includes an absorption of light by the fat, the muscle, or the interstitial fluid.

* * * * *